United States Patent [19]
Ebling et al.

[11] Patent Number: 5,810,790
[45] Date of Patent: Sep. 22, 1998

[54] CATHETER WITH VIEWING SYSTEM AND PORT CONNECTOR

[76] Inventors: Wendell V. Ebling, 21131 Kensington La., Lake Forest, Calif. 92630; Theodore Leonard Hendrickson, 4174 Trail Crest Dr., Moorpark, Calif. 93021

[21] Appl. No.: 753,108

[22] Filed: Nov. 19, 1996

[51] Int. Cl.⁶ .................................................. A61M 25/00
[52] U.S. Cl. .............................. 604/280; 604/96; 604/283
[58] Field of Search .................................... 604/280, 264, 604/283, 96, 102, 20, 21; 128/633, 634; 606/2, 13–16, 7; 600/101, 115, 116

[56] References Cited

U.S. PATENT DOCUMENTS

| | | | |
|---|---|---|---|
| Re. 33,166 | 2/1990 | Samson | 606/194 |
| Re. 33,854 | 3/1992 | Adair | 128/6 |
| 1,680,490 | 8/1928 | Wappler | |
| 2,067,031 | 1/1937 | Wappler | 128/7 |
| 2,129,391 | 9/1938 | Wappler | 128/6 |
| 2,541,976 | 2/1951 | Bogart | 250/503.1 |
| 2,691,370 | 10/1954 | Wallace | 128/6 |
| 2,922,415 | 1/1960 | Campagna | 128/4 |
| 2,975,785 | 3/1961 | Sheldon | 128/6 |
| 2,990,830 | 7/1961 | Hett | 128/4 |
| 3,043,309 | 7/1962 | McCarthy | 128/348 |
| 3,144,020 | 8/1964 | Zingale | 128/4 |
| 3,162,190 | 12/1964 | Del Gizzo | 128/6 |
| 3,373,736 | 3/1968 | Fiore et al. | 128/6 |
| 3,470,876 | 10/1969 | Barchilon | 128/348 |
| 3,485,237 | 12/1969 | Bedford | 128/2 |
| 3,495,586 | 2/1970 | Regenbogen | 128/6 |
| 3,521,620 | 7/1970 | Cook | 128/2.05 |
| 3,547,103 | 12/1970 | Cook | 128/2.05 |
| 3,605,725 | 9/1971 | Bentov | 128/2.05 |
| 3,625,200 | 12/1971 | Muller | 128/2.05 |
| 3,636,940 | 1/1972 | Gravlee | 128/2 |
| 3,674,014 | 7/1972 | Tillander | 128/2 |
| 3,720,203 | 3/1973 | Brown | 128/4 |
| 3,729,008 | 4/1973 | Berkovits | 128/418 |
| 3,757,768 | 9/1973 | Kline | 128/2 |
| 3,773,034 | 11/1973 | Burns et al. | 128/2 |
| 3,794,091 | 2/1974 | Ersek et al. | 150/52 R |
| 3,809,072 | 5/1974 | Ersek et al. | 128/23 |
| 3,866,601 | 2/1975 | Russell | 128/4 |
| 3,890,977 | 6/1975 | Wilson | 128/418 |
| 3,945,371 | 3/1976 | Adelman | 128/2 |
| 3,947,089 | 3/1976 | Rapp | 350/151 |
| 3,980,078 | 9/1976 | Tominaga | 128/4 |
| 4,033,331 | 7/1977 | Guss et al. | 128/2 |
| 4,040,413 | 8/1977 | Ohshiro | 128/6 |
| 4,076,018 | 2/1978 | Heckele | 128/6 |
| 4,085,742 | 4/1978 | Okada | 128/4 |
| 4,132,227 | 1/1979 | Ibe | 128/4 |
| 4,146,019 | 3/1979 | Bass et al. | 128/6 |
| 4,176,662 | 12/1979 | Frazer et al. | 128/6 |
| 4,201,199 | 5/1980 | Smith | 128/7 |
| 4,243,049 | 1/1981 | Goodale et al. | 128/757 |
| 4,248,214 | 2/1981 | Hannah et al. | 128/7 |
| 4,249,533 | 2/1981 | Komiya | 128/303.1 |
| 4,254,762 | 3/1981 | Yoon | 128/4 |
| 4,327,735 | 5/1982 | Hampson | 128/348 |
| 4,329,995 | 5/1982 | Anthracite | 128/350 |
| 4,375,818 | 3/1983 | Suwaki et al. | 128/660 |
| 4,389,208 | 6/1983 | LeVeen et al. | 604/95 |

(List continued on next page.)

FOREIGN PATENT DOCUMENTS 193885  1/1965  Sweden .

*Primary Examiner*—Corrine M. McDermott
*Assistant Examiner*—Cris L. Rodriguez
*Attorney, Agent, or Firm*—Stetina Brunda Garred & Brucker

[57] ABSTRACT

A balloon-retention catheter for insertion into a chamber of a living being. The catheter includes a length of catheter tubing having an inflatable balloon immediately behind the distal end. Within the tubing is a fluid lumen, a balloon inflation lumen, and a third lumen to accommodate an endoscope whose distal end projects beyond the distal end of the catheter tubing. Accommodation of an endoscope permits required longevity of use of the catheter without its removal and reintroduction each time a visual inspection is indicated.

8 Claims, 1 Drawing Sheet

U.S. PATENT DOCUMENTS

| | | | |
|---|---|---|---|
| 4,401,123 | 8/1983 | Baba | 128/660 |
| 4,403,985 | 9/1983 | Boretos | 604/53 |
| 4,445,892 | 5/1984 | Hussein et al. | 604/101 |
| 4,448,188 | 5/1984 | Loeb | 128/6 |
| 4,456,017 | 6/1984 | Miles | 128/772 |
| 4,470,407 | 9/1984 | Hussein | 128/6 |
| 4,538,622 | 9/1985 | Samson et al. | 128/772 |
| 4,543,090 | 9/1985 | McCoy | 604/95 |
| 4,545,390 | 10/1985 | Leary | 128/772 |
| 4,554,929 | 11/1985 | Samson et al. | 128/772 |
| 4,576,145 | 3/1986 | Tsuno et al. | 128/6 |
| 4,581,017 | 4/1986 | Sahota | 604/101 |
| 4,582,181 | 4/1986 | Samson | 128/348.1 |
| 4,586,923 | 5/1986 | Gould et al. | 604/95 |
| 4,601,705 | 7/1986 | McCoy | 604/95 |
| 4,616,653 | 10/1986 | Samson et al. | 128/344 |
| 4,624,243 | 11/1986 | Lowery et al. | 128/6 |
| 4,627,436 | 12/1986 | Leckrone | 128/303.1 |
| 4,631,052 | 12/1986 | Kensey | 604/22 |
| 4,641,654 | 2/1987 | Samson et al. | 128/344 |
| 4,646,722 | 3/1987 | Silverstein et al. | 128/4 |
| 4,647,149 | 3/1987 | McCartney et al. | 350/96.2 |
| 4,650,466 | 3/1987 | Luther | 604/95 |
| 4,654,024 | 3/1987 | Crittenden et al. | 604/49 |
| 4,669,465 | 6/1987 | Moore et al. | 128/303.1 |
| 4,676,249 | 6/1987 | Arenas et al. | 128/657 |
| 4,685,449 | 8/1987 | Bonnet | 128/4 |
| 4,690,175 | 9/1987 | Ouchi et al. | 138/131 |
| 4,694,828 | 9/1987 | Eichenbaum | 128/303.1 |
| 4,710,176 | 12/1987 | Quick | 604/177 |
| 4,719,924 | 1/1988 | Crittenden et al. | 128/772 |
| 4,721,097 | 1/1988 | D'Amello | 128/4 |
| 4,721,117 | 1/1988 | Mar et al. | 128/772 |
| 4,723,936 | 2/1988 | Buchbinder | 604/95 |
| 4,724,846 | 2/1988 | Evans | 128/772 |
| 4,726,369 | 2/1988 | Mar | 128/303 |
| 4,741,326 | 5/1988 | Sidall | 128/4 |
| 4,742,817 | 5/1988 | Kawashima | 128/4 |
| 4,748,981 | 6/1988 | Crittenden | 128/344 |
| 4,748,982 | 6/1988 | Horzewski | 128/344 |
| 4,757,381 | 7/1988 | Cooper | 358/98 |
| 4,757,827 | 7/1988 | Buchbinder et al. | 128/772 |
| 4,758,222 | 7/1988 | McCoy | 604/95 |
| 4,763,647 | 8/1988 | Gambale | 128/657 |
| 4,765,314 | 8/1988 | Kolditz et al. | 128/4 |
| 4,770,653 | 9/1988 | Shturman | 128/21 |
| 4,772,275 | 9/1988 | Erlich | 604/280 |
| 4,775,371 | 10/1988 | Mueller | 604/280 |
| 4,776,340 | 10/1988 | Moran et al. | 128/634 |
| 4,779,611 | 10/1988 | Grooters et al. | 128/4 |
| 4,798,598 | 1/1989 | Bonello et al. | 604/280 |
| 4,813,400 | 3/1989 | Washizuka et al. | 128/6 |
| 4,813,434 | 3/1989 | Buchbinder et al. | 128/772 |
| 4,815,478 | 3/1989 | Buchbinder et al. | 128/772 |
| 4,820,349 | 4/1989 | Saab | 128/344 |
| 4,827,941 | 5/1989 | Taylor et al. | 128/657 |
| 4,832,047 | 5/1989 | Sepetka et al. | 128/772 |
| 4,836,187 | 6/1989 | Iwakoshi et al. | 128/4 |
| 4,841,952 | 6/1989 | Sato et al. | 128/6 |
| 4,846,186 | 7/1989 | Box et al. | 128/657 |
| 4,846,193 | 7/1989 | Tremulis et al. | 128/772 |
| 4,850,351 | 7/1989 | Herman et al. | 128/303.1 |
| 4,858,001 | 8/1989 | Milbank et al. | 358/98 |
| 4,860,731 | 8/1989 | Matsuura | 128/6 |
| 4,869,238 | 9/1989 | Opie | 128/6 |
| 4,875,481 | 10/1989 | Higgins | 128/344 |
| 4,875,489 | 10/1989 | Messner et al. | 128/772 |
| 4,877,031 | 10/1989 | Conway et al. | 128/344 |
| 4,886,067 | 12/1989 | Palermo | 128/657 |
| 4,889,106 | 12/1989 | Watanabe | 128/4 |
| 4,892,099 | 1/1990 | Ohkawa et al. | 606/194 |
| 4,892,519 | 1/1990 | Songer et al. | 604/96 |
| 4,907,395 | 3/1990 | Opie et al. | 53/434 |
| 4,911,148 | 3/1990 | Sosnowski et al. | 128/6 |
| 4,916,534 | 4/1990 | Takahashi et al. | 358/98 |
| 4,921,482 | 5/1990 | Hammerslag et al. | 604/95 |
| 4,934,340 | 6/1990 | Ebling et al. | 128/6 |
| 4,960,411 | 10/1990 | Buchbinder | 604/95 |
| 4,979,498 | 12/1990 | Oneda et al. | 128/6 |
| 4,986,257 | 1/1991 | Chikama | 128/4 |
| 4,997,084 | 3/1991 | Opie et al. | 206/364 |
| 4,998,527 | 3/1991 | Meyer | 128/6 |
| 4,998,916 | 3/1991 | Hammerslag et al. | 604/95 |
| 5,002,041 | 3/1991 | Chikama | 128/4 |
| 5,030,227 | 7/1991 | Rosenbluth et al. | 606/192 |
| 5,031,603 | 7/1991 | Gautier et al. | 128/4 |
| 5,037,391 | 8/1991 | Hammerslag et al. | 604/95 |
| 5,041,108 | 8/1991 | Fox et al. | 606/7 |
| 5,090,959 | 2/1992 | Samson et al. | 604/96 |
| 5,108,368 | 4/1992 | Hammerslag | 604/95 |
| 5,116,317 | 5/1992 | Carson, Jr. et al. | 604/96 |
| 5,127,393 | 7/1992 | McFarlin et al. | 128/4 |
| 5,152,277 | 10/1992 | Honda et al. | 128/4 |
| 5,156,590 | 10/1992 | Vilmar | 604/4 |
| 5,163,950 | 11/1992 | Pinchuk et al. | 606/192 |
| 5,186,596 | 2/1993 | Condon et al. | 604/101 |
| 5,188,094 | 2/1993 | Adair | 128/6 |
| 5,193,525 | 3/1993 | Silverstein et al. | 128/4 |
| 5,213,093 | 5/1993 | Swindle | 128/4 |
| 5,230,621 | 7/1993 | Jacoby | 433/29 |
| 5,235,283 | 8/1993 | Lehne et al. | 324/318 |
| 5,255,668 | 10/1993 | Umeda | 128/4 |
| 5,285,795 | 2/1994 | Ryan et al. | 128/750 |
| 5,328,365 | 7/1994 | Jacoby | 433/29 |
| 5,335,647 | 8/1994 | Brustad | 128/4 |
| 5,344,419 | 9/1994 | Spears | 606/15 |
| 5,347,990 | 9/1994 | Ebling et al. | 128/4 |
| 5,370,640 | 12/1994 | Kolff | 606/2 |
| 5,417,653 | 5/1995 | Sakota et al. | 604/20 |
| 5,437,637 | 8/1995 | Lieber et al. | 604/96 |
| 5,443,057 | 8/1995 | Elmore | 600/133 |
| 5,466,234 | 11/1995 | Loeb et al. | 606/15 |
| 5,536,234 | 7/1996 | Newman | 600/104 |
| 5,569,161 | 10/1996 | Ebling et al. | 600/121 |

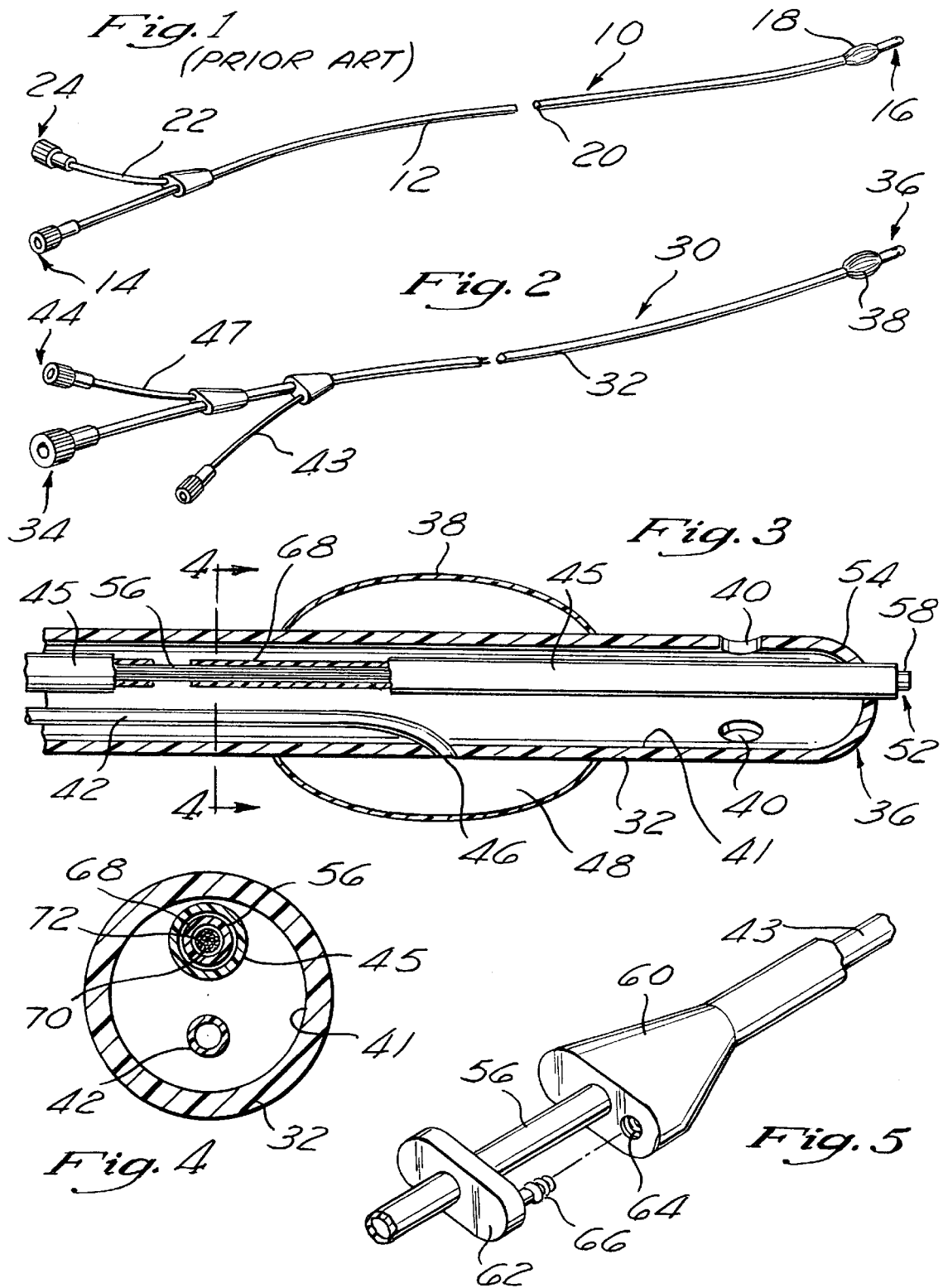

CATHETER WITH VIEWING SYSTEM AND PORT CONNECTOR

FIELD OF THE INVENTION

The present invention relates in general to catheters, and in particular to a catheter having a distal balloon retention member and an inner lumen within- which an endoscope can be housed for simultaneous insertion through an orifice into a chamber of a living being for diagnostic viewing.

BACKGROUND OF THE INVENTION

A typical fluid delivery and fluid collection catheter is one having an inflatable balloon near its distal end for retention of the catheter at a particular location. Probably the most common catheter of this type is the Foley catheter. In particular, a Foley catheter is typically used for entry into the urinary bladder to accomplish urine flow therefrom and to introduce medication into the bladder. Patients requiring such treatment generally must have the catheter in place for a period of time. As a result, once the catheter is in place and the balloon is just beyond the neck of the bladder, the balloon is inflated to thereby secure the catheter and prevent its outward passage.

If medical treatment within the bladder of a catherized patient is required, it many times is necessary for a physician to inspect the interior thereof with an endoscope. To accomplish insertion of the endoscope obviously requires removal of the catheter and subsequent insertion of the endoscope through the urethra. After viewing, the endoscope must be removed and the catheter once again inserted. These insertion and removal procedures are unpleasant and possibly painful, are time consuming, and certainly interfere with ongoing internal observations at will.

In view of these limitations on patient treatment, it is apparent that a need is present for instrumentation that can permit continued treatment while observations of treated areas can simultaneously occur. It is therefore a primary object of the present invention to provide a balloon-retained catheter having a designated additional lumen to house an endoscope.

Another object of the present invention is to provide such a balloon-retained catheter wherein the endoscope can be releasably retained.

Yet another object of the present invention is to provide a balloon-retained catheter system wherein an endoscope situated within a lumen of the catheter can be encased in a sterile sleeve such that the endoscope itself need not be sterilized prior to use.

These and other objects of the present invention will become apparent throughout the description which now follows.

SUMMARY OF THE INVENTION

The present invention is a balloon-retention catheter for insertion into a chamber of a living being. In particular, the catheter comprises a length of catheter tubing having a proximal end and a distal end, with the distal end thereof having immediately there behind an inflatable balloon surrounding a portion of the tubing. The catheter has a first lumen having an open proximal end and an open distal end and extends through the tubing from the proximal end to the distal end for conveying fluid therethrough. The catheter additionally has a second lumen having an open proximal end and an open distal end extending through at least a portion of the tubing to terminate distally at an interior site of the balloon for conveying inflation fluid to and from the balloon, and a third lumen having an open proximal end and an open distal end and extending through at least a portion of the tubing to terminate at the distal end of the tubing. The third lumen is constructed to accommodate an endoscope having a distal end such that the distal end of the endoscope will project beyond the distal end of the tubing. When an endoscope is in place, its distal end projects minimally beyond the distal end of the catheter, with such projection distance being no more than is necessary to effectuate desired viewability of tissue. The endoscope can be encased within a sterile sleeve so that the fiber optic image bundle of the endoscope need not be sterilized prior to any use.

The present invention provides a significant advance in both patient comfort and disease diagnosis. As is evident, incorporation of a lumen within a balloon-retained catheter to accommodate an endoscope permits required longevity of use of the catheter without its removal and reintroduction each time a visual inspection is indicated.

BRIEF DESCRIPTION OF THE DRAWINGS

An illustrative and presently preferred embodiment of the invention is shown in the accompanying drawings in which:

FIG. 1 is a side elevation view of a prior art balloon-retained catheter;

FIG. 2 is a side elevation view of a balloon-retained catheter having a lumen for accommodating an endoscope;

FIG. 3 is an enlarged cross sectional view of the distal portion of the catheter as shown in FIG. 2;

FIG. 4 is a cross sectional view taken along line 4—4 of FIG. 3; and

FIG. 5 is an enlarged view of the releasable connector members for releasable engagement of the proximal ends of the endoscope and its lumen structure.

DETAILED DESCRIPTION OF THE PREFERRED EMBODIMENT

Referring to FIG. 1, a prior-art balloon-retained catheter 10, here being a Foley catheter, is shown. The catheter 10 includes a length of tubing 12 having an open proximal end 14 and an open distal end 16, with the distal opening including laterally disposed apertures. Immediately behind the distal end 16 is an inflatable balloon 18 surrounding a portion of the tubing 12. A first lumen 20 defined by the tubing 12 extends from the proximal end 14 to the distal end 16 thereof for conveying fluid therethrough. A second lumen 22 is disposed within the tubing 12 and is accessible via an open proximal end 24. The second lumen 22 leads to the interior of the balloon 18 for passage of fluid for balloon inflation and deflation.

Referring now to FIGS. 2 through 5, a balloon-retained catheter 30 is shown wherein an endoscope can be retained. The catheter 30 is identical to the prior art catheter 10 of FIG. 1, except with the capability of housing an endoscope as hereafter described. Thus, the catheter 30 includes a length of tubing 32 having an open proximal end 34 and an open distal end 36, with the distal end opening being four uniformally laterally disposed apertures as exemplified by aperture 40. Immediately behind the distal end 36 is an inflatable balloon 38 surrounding a portion of the tubing 32. A first lumen 41 defined by the tubing 32 extends from the proximal end 34 to the distal end 36 for conveying fluid therethrough. A second lumen 42 is disposed within the tubing 32 and is accessible via an open proximal end 44 situated in connector tubing 47. The second lumen 42 has an open distal end 46 leading to the interior 48 of the balloon 38 for passage of fluid to inflate or deflate the balloon 38.

A third lumen 45 is disposed within the tubing 32 and is accessible via an open proximal end 50 situated distally from the proximal end of the tubing 32 in lateral connector tubing 43. The third lumen 45 has an open distal end 52 at the distal tip 54 of the tubing 32, and accommodates an endoscope 56 such that the distal end 58 of the endoscope 56 projects beyond the distal tip 54 a distance sufficient to provide beneficial viewing. As shown in FIG. 5, the open proximal end 50 of the lateral connector tubing 43 may be defined by a port connector 60 complimentarily engageable with an endoscope connector 62 of the endoscope 56. In the embodiment shown, the port connector 60 has a receptor channel 64 within which a projection 66 of the connector 62 is releasably received by friction fit. The endoscope 56 itself can be encased in a sterile sleeve 68, as generally described in U.S. Pat. No. 5,347,990, to thereby eliminate the need to sterilize the endoscope itself. Thus, as shown in FIG. 3, for example, the endoscope assembly comprises a fiber bundle 70 having a sheath 72 thereabout inside the sleeve 68. At least the distal end of the sleeve 68 is transparent to thereby permit viewing of the endoscope 56.

Operation of the catheter 30 is commenced by first positioning the distal end 36 at a desired site usually within a cavity such as a urinary bladder. When desired placement is attained, fluid such as a saline solution is introduced into the second lumen 42 for travel to the interior 48 of the balloon 38 and inflation thereof and retention of the catheter 30 in place. Once so situated, the catheter 30 permits free fluid flow from and/or to the site of its distal end 36. To visually inspect the site of the distal end 36 of the catheter 30, an endoscope 56 is inserted into the third lumen 45 and advanced until its distal end 58 resides beyond the distal tip 54 of the tubing 32. Such advancement results in engagement of the port connector 60 and endoscope connector 62 for releasable retention of the endoscope 56 for use in viewing the catherized site. In this manner, a physician or other healthcare worker can endoscopically view a site without first removing a catheterized site. In this manner, a physician or other healthcare worker can endoscopically view a site without first removing a catheter treating that site.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

What is claimed is:

1. A urinary catheter, comprising:

an elongate catheter tube having proximal and distal ends, said catheter tube defining a first lumen for conveying fluid therethrough;

an inflatable balloon attached to and extending at least partially about the catheter tube adjacent the distal end thereof;

an inflation tube extending within the first lumen and having a proximal end and a distal end which is in fluid communication with the interior of the balloon, the inflation tube defining a second lumen for conveying inflation fluid to and from the balloon;

an endoscope tube extending within the first lumen and having a proximal end and a distal end which protrudes from the distal end of the catheter tube, the endoscope tube defining a third lumen;

an elongate endoscope slidably disposed within the third lumen, said endoscope having proximal and distal ends and a connector including a projection extending therefrom; and a port connector attached to the proximal end of the endoscope tube, said port connector including an opening for allowing passage of the endoscope into the third lumen and a receptor channel for receiving the projection of the connector of the endoscope;

wherein the receipt of the projection into the receptor channel occurring as a result of the proximal advancement of the endoscope within the third lumen effectively locks the endoscope in a position within the third lumen whereat the distal end of the endoscope protrudes from the distal end of the endoscope tube.

2. The urinary catheter of claim 1 wherein the catheter tube includes at least one flow aperture disposed therein adjacent the distal end thereof.

3. The urinary catheter of claim 2 wherein the catheter tube includes multiple flow apertures disposed therein adjacent the distal end thereof.

4. The urinary catheter of claim 1 wherein the endoscope is encased in a sterile sleeve.

5. A urinary catheter, comprising:

an elongate catheter tube having proximal and distal ends, said catheter tube defining a first lumen for conveying fluid therethrough;

an endoscope tube extending within the first lumen and having a proximal end and a distal end which terminates at the distal end of the catheter tube, said endoscope tube defining a third lumen;

an elongate endoscope slidably disposed within the third lumen, said endoscope having proximal and distal ends and a connector including a projection extending therefrom; and a port connector attached to the proximal end of the endoscope tube, said port connector including an opening for allowing passage of the endoscope into the third lumen and a receptor channel for receiving the projection of the connector of the endoscope;

wherein the receipt of the projection into the receptor channel occurring as a result of the proximal advancement of the endoscope within the third lumen effectively locks the endoscope in a position within the third lumen whereat the distal end of the endoscope protrudes from the distal end of the endoscope tube and the distal end of the catheter tube.

6. The urinary catheter of claim 5 wherein the catheter tube includes at least one flow aperture disposed therein adjacent the distal end thereof.

7. The urinary catheter of claim 6 wherein the catheter tube includes multiple flow apertures disposed therein adjacent the distal end thereof.

8. The urinary catheter of claim 5 wherein the endoscope is encased in a sterile sleeve.

* * * * *